US012640263B2

(12) United States Patent
Chavarukattil et al.

(10) Patent No.: US 12,640,263 B2
(45) Date of Patent: May 26, 2026

(54) GENERATIVE ARTIFICIAL INTELLIGENCE DRIVEN SELF-HEALING AGENT FOR MEDICAL DEVICES

(71) Applicant: GE Precision Healthcare LLC, Waukesha, WI (US)

(72) Inventors: Mathews Matson Chavarukattil, Bangalore (IN); Rama Krishna Reddy Narayana Reddy Gari, Bangalore (IN); Sridhar Madhavan, Barrington, IL (US); Sai Kumar Muppalla, Bangalore (IN); Manjunath Janardhan, Bangalore (IN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 41 days.

(21) Appl. No.: 18/749,679

(22) Filed: Jun. 21, 2024

(65) Prior Publication Data

US 2025/0391550 A1 Dec. 25, 2025

(51) Int. Cl.
_G16H 40/40_ (2018.01)
(52) U.S. Cl.
CPC .................................. _G16H 40/40_ (2018.01)
(58) Field of Classification Search
CPC ...................................................... G16H 40/40
See application file for complete search history.

(56) References Cited

U.S. PATENT DOCUMENTS

| 7,055,062 B2 | 5/2006 | Shah et al. |
| 8,015,443 B2 | 9/2011 | Adachi |

| 9,375,201 B2 | 6/2016 | Mercer et al. | |
| 10,102,082 B2 | 10/2018 | Caberera et al. | |
| 11,221,617 B2 * | 1/2022 | Yu ........................ | G06N 3/0499 |
| 11,457,888 B2 | 10/2022 | Uebler | |
| 11,707,250 B2 | 7/2023 | Campagna et al. | |
| 2020/0209109 A1 | 7/2020 | Liang et al. | |
| 2021/0064932 A1 | 3/2021 | Wang et al. | |

(Continued)

FOREIGN PATENT DOCUMENTS

| CN | 111078845 A * | 4/2020 | ............. H04L 51/02 |
| JP | 2008149151 | 7/2008 | |

OTHER PUBLICATIONS

Salomone, Ivan. "Leveraging the enterprise knowledge graph for predictive maintenance." Master's Dissertation. 2021. https://www.um.edu.mt/library/oar/handle/123456789/91915 (Year: 2021).*

(Continued)

*Primary Examiner* — Linh Giang Le

(74) *Attorney, Agent, or Firm* — Fletcher Yoder, P.C.

(57) ABSTRACT

A medical device includes a memory encoding processor-executable routines. The medical device also includes a processing system including one or more processors and is configured to access the memory and to execute the processor-executable routines, wherein the routines, when executed by the processing system, cause the processing system to perform actions. The actions include utilizing an autonomous self-healing agent framework, via generative artificial intelligence based reasoning, to detect an issue with the medical device, to locate an appropriate fix for the issue, and to implement the appropriate fix to resolve the issue.

11 Claims, 11 Drawing Sheets

10

| Machine - Artificial Intelligence | |
|---|---|
| When Everything is OK | Machine Function Normally |
| When Something Goes Wrong | Machine Knows What the Symptom is (Auto Detection Using Indicators Such as Sensors/Log Signatures - Table Moving Slowly etc) |
| Detection | Machine Can Check Using Some Tools - eg: Diagnostic Tool |
| Isolation and Recovery | Machine Can Self-Heal - Isolation and Recovery |
| Escalation | Machine Can Auto-Generate and SR and Get an FE to Help |
| Resolution | Machine Gets Fixed by FE - Parts Change |

(56)                    References Cited

U.S. PATENT DOCUMENTS

2022/0103421 A1* 3/2022 Singh .................. H04L 41/0661
2024/0346256 A1* 10/2024 Qin ........................ G06F 40/216

OTHER PUBLICATIONS

U.S. Appl. No. 18/628,382, filed Apr. 5, 2024, Rama Krishna Reddy
Narayana Reddy Gari.
U.S. Appl. No. 18/422,591, filed Jan. 25, 2024, Sridhar Madhavan.

* cited by examiner

| Machine - Artificial Intelligence | |
|---|---|
| When Everything is OK | Machine Function Normally |
| When Something Goes Wrong | Machine Knows What the Symptom is (Auto Detection Using Indicators Such as Sensors/Log Signatures - Table Moving Slowly etc) |
| Detection | Machine Can Check Using Some Tools - eg: Diagnostic Tool |
| Isolation and Recovery | Machine Can Self-Heal - Isolation and Recovery |
| Escalation | Machine Can Auto-Generate and SR and Get an FE to Help |
| Resolution | Machine Gets Fixed by FE - Parts Change |

GENERATIVE ARTIFICIAL INTELLIGENCE DRIVEN SELF-HEALING AGENT FOR MEDICAL DEVICES

BACKGROUND

The subject matter disclosed herein relates to a generative artificial intelligence (AI) driven self-healing agent for medical devices.

When medical devices go down, it can be very costly when there are critical patients waiting for its use. Hence, it is important to quickly get the devices operative again. Most of the time, these devices are equipped with tools to diagnose and to fix the failures. However, a human expert is required to look at the symptom and to decide on which tool to run. Many times, the steps to diagnose and to fix the issues are listed in service manuals. A remote or field engineer looks through the service manuals and manually troubleshoots, diagnoses, and fixes the medial device.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a medical device is provided. The medical device includes a memory encoding processor-executable routines. The medical device also includes a processing system including one or more processors and is configured to access the memory and to execute the processor-executable routines, wherein the routines, when executed by the processing system, cause the processing system to perform actions. The actions include utilizing an autonomous self-healing agent framework, via generative artificial intelligence based reasoning, to detect an issue with the medical device, to locate an appropriate fix for the issue, and to implement the appropriate fix to resolve the issue.

In another embodiment, a computer-implemented method for a medical device to self-heal is provided. The computer-implemented method includes utilizing an autonomous self-healing agent framework stored on a medical device, via generative artificial intelligence based reasoning, to detect an issue with the medical device, to locate an appropriate fix for the issue, and to implement the appropriate fix to resolve the issue.

In a further embodiment, a non-transitory computer-readable medium is provided. The non-transitory computer-readable medium include processor-executable code that when executed by a processing system including one or more processors, causes the processing system to perform actions. The actions include utilizing an autonomous self-healing agent framework stored on a device, via generative artificial intelligence based reasoning, to detect an issue with the medical device, to locate an appropriate fix for the issue, and to implement the appropriate fix to resolve the issue.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 1 is a table illustrating how machine artificial intelligence can be utilized in servicing a medical device, in accordance with aspects of the present disclosure;

DETAILED DESCRIPTION

Figure 2:
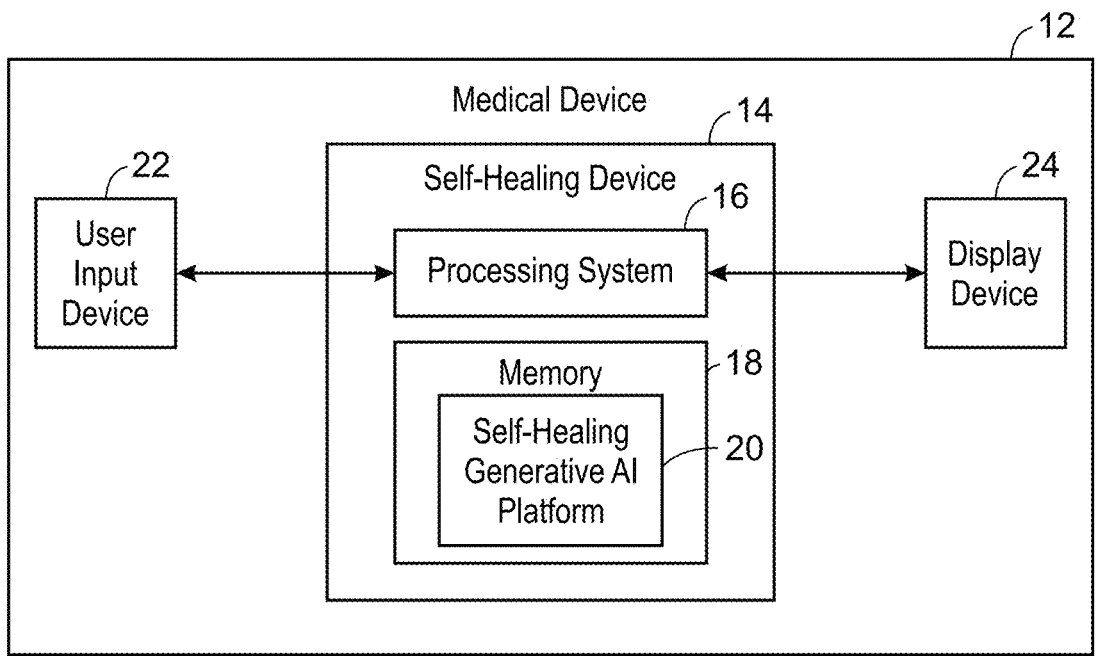
FIG. 2 is a schematic diagram of medical device configured to self-heal, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

The term processor, processing system, or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

As used herein, the term "computing system" refers to an electronic computing device such as, but not limited to, a single computer, virtual machine, virtual container, host, server, laptop, and/or mobile device, or to a plurality of electronic computing devices working together to perform the function described as being performed on or by the computing system. As used herein, the terms "application", "application module" (or "module"), "engine", or "program", or "plugin" refers to one or more sets of computer software instructions (e.g., computer programs and/or scripts) executable by one or more processors of a computing system to provide particular functionality. Computer software instructions can be written in any suitable programming languages, such as C, C++, C#, Pascal, Fortran, Perl, MATLAB, SAS, SPSS, JavaScript, AJAX, and JAVA. Such computer software instructions can comprise an independent application with data input and data display aspects (e.g., modules). Alternatively, the disclosed computer software instructions can be classes that are instantiated as distributed objects. The disclosed computer software instructions can also be component software, for example JAVABEANS or ENTERPRISE JAVABEANS. Additionally, the disclosed applications or engines can be implemented in computer software, computer hardware, or a combination thereof.

As used herein, the terms "automatic" and "automatically" refer to actions that are performed by a computing device or computing system (e.g., of one or more computing devices) without human intervention. For example, automatically performed functions may be performed by computing devices or systems based solely on data stored on and/or received by the computing devices or systems despite the fact that no human users have prompted the computing devices or systems to perform such functions. As but one non-limiting example, the computing devices or systems may make decisions and/or initiate other functions based solely on the decisions made by the computing devices or systems, regardless of any other inputs relating to the decisions.

As used herein, the term "medical device" refers to any medical equipment or medical systems that utilize a computing system and that typically may require a field engineer for servicing. For example, the medical device may include patient monitoring systems, care providing systems, and medical imaging systems (e.g., computed tomography imaging system, digital radiography system, ultrasound imaging system, magnetic resonance imaging system, nuclear medicine imaging system, etc.) are some non-limiting examples.

Deep learning (DL) approaches discussed herein may be based on artificial neural networks, and may therefore encompass one or more of deep neural networks, fully connected networks, convolutional neural networks (CNNs), transformer-based networks, unrolled neural networks, perceptrons, encoders-decoders, recurrent networks, wavelet filter banks, u-nets, general adversarial networks (GANs), dense neural networks, or other neural network architectures. The neural networks may include shortcuts, activations, batch-normalization layers, and/or other features. These techniques are referred to herein as DL techniques, though this terminology may also be used specifically in reference to the use of deep neural networks, which is a neural network having a plurality of layers.

As discussed herein, DL techniques (which may also be known as deep machine learning, hierarchical learning, or deep structured learning) are a branch of machine learning techniques that employ mathematical representations of data and artificial neural networks for learning and processing such representations. By way of example, DL approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

When a medical device goes down, it may take significant time (e.g., days) to get a service engineer to come out and to service the medical device. In addition, connectivity with a medical device may pose challenges in serving the medical device. Further, health care facilities (e.g., hospitals) may be hesitant to provide a field engineer to access the medical device. With the advent of generative AI and an autonomous agent framework, it possible to reason through service manual procedures and the guide the machine (i.e., medical device) or the technologist in self-healing the medical device without the involvement of service engineers.

The present disclosure provides for systems and methods for a medical device to self-heal. In particular, a generative AI based self-healing agent framework is located on the medical device and is utilized to self-heal the medical device. The features of the self-healing agent framework include utilizing generative AI based reasoning in utilizing troubleshooting procedures for the medical device. The features of the self-healing agent framework also includes utilizing autonomous agents to utilize diagnostic and fixing tools provided by the original equipment manufacturer of the medical device.

The disclosed embodiments include a medical system that includes a memory encoding processor-executable routines. The medical device also includes a processing system including one or more processors and is configured to access the memory and to execute the processor-executable routines, wherein the routines, when executed by the processing system, cause the processing system to perform actions. The actions include utilizing an autonomous self-healing agent framework, via generative artificial intelligence based reasoning, to detect an issue with the medical device, to locate (e.g., find or determine) an appropriate fix for the issue, and to implement the appropriate fix to resolve the issue.

In certain embodiments, the autonomous self-healing agent framework includes a tool augmented large language model. In certain embodiments, the processing system is configured to initiate utilization of the autonomous self-healing agent framework for healing in response to detecting an indicator (e.g., system indicator) of the issue from the medical device via a system bot. In certain embodiments, the processing system is configured to initiate utilization of the autonomous self-healing agent framework for healing in response to receiving user input, via a user bot, to initiate the utilization.

In certain embodiments, the autonomous self-healing agent framework is configured to access and to utilize tools and functions provided by an original equipment manufacturer of the medical device in a service application program interface in fixing the issue. In certain embodiments, the tools and functions include a detection agent, a recovery agent, and monitors.

In certain embodiments, the autonomous self-healing agent framework is configured to access a knowledge graph and to utilize generative artificial intelligence in reasoning through the knowledge graph to detect the issue with the medical device and to locate (e.g., find or determine) the appropriate fix for the issue. In certain embodiments, nodes of the knowledge graph include service manuals for the medical device, tool descriptions, fault tree analysis, and failure modes and effects analysis.

In certain embodiments, the autonomous self-healing agent framework is configured to access a memory when utilizing generative artificial intelligence in reasoning through the knowledge graph to detect the issue with the medical device and to locate (e.g., find or determine) the appropriate fix for the issue. In certain embodiments, the autonomous self-healing agent framework is configured to store in the memory a record of detecting the issue with the medical device and fixing the issue. In certain embodiments, the autonomous self-healing agent framework is configured to automatically generate a service request when the issue cannot be resolved by the autonomous self-healing agent framework.

The disclosed embodiments reduce the downtime of medical device. The disclosed embodiments improve service productivity by eliminating the involvement of a remote/field service engineer in fixing the medical device failures.

With the preceding in mind, and by way of providing useful context, FIG. 1 depicts a table 10 illustrating how machine artificial intelligence can be utilized in servicing a medical device (i.e., medical device in table 10). For example, as depicted in the table 10, in the scenario when everything is okay, the machine functions normally. In the scenario when something goes wrong, the machine knows what the symptom is. For example, the knows what the symptom is (e.g., table is moving slowly) via auto detection using indicators from sensors and/or long signatures. With regard to detection, the machine can itself using tools (e.g., diagnostic tools). With regard to isolation and recovery, the system can self-heal. With regard to escalation, the machine can autogenerate a service request to get help from a service/field engineer when the machine cannot fix itself. With regard to resolution, the machine can get fixed by the service/field engineer (e.g., via changing a part).

FIG. 2 is a schematic diagram of a medical device 12 that is configured to self-heal. As noted above, the medical device 12 may be any medical equipment or medical systems that utilize a computing system and that typically may require a field engineer for servicing. For example, the medical device may include patient monitoring systems, care providing systems, and medical imaging systems (e.g., computed tomography imaging system, digital radiography system, ultrasound imaging system, magnetic resonance imaging system, nuclear medicine imaging system, etc.) are some non-limiting examples.

As depicted, the medical device 12 includes a self-healing device 14 (e.g., implemented in a computing device) located on the medical device 12 (e.g., located within a housing of the medical device 12). The self-healing device 14 is configured to utilize an autonomous self-healing agent framework, via generative artificial intelligence based reasoning, to detect an issue with the medical device 12, to locate (e.g., find or determine) an appropriate fix for the issue, and to implement the appropriate fix to resolve the issue.

The self-healing device 14 includes one or more processors forming a processing system 16 configured to execute machine readable instructions stored in non-transitory memory 18. A processor of the processing system 16 may be single core or multi-core, and the programs executed thereon may be configured for parallel or distributed processing. In some embodiments, the processing system 16 may optionally include individual components that are distributed throughout two or more devices, which may be remotely located and/or configured for coordinated processing. In some embodiments, one or more aspects of the processing system 16 may be virtualized and executed by remotely-accessible networked computing devices configured in a cloud computing configuration.

The self-healing device also includes the non-transitory memory 18. The non-transitory memory 18 may store a self-healing generative AI platform 20. The self-healing generative AI platform is configured to detect an issue with the medical device 12, to locate (e.g., find or determine) an appropriate fix for the issue, and to implement the appropriate fix on the medical device 12 to resolve the issue. In certain embodiments, the self-healing generative AI platform 20, when it cannot resolve the issue, autogenerates a service request for a service/field engineer to service the medical device 12. In certain embodiments, the self-healing generative AI platform 20 is configured to provide instruction to the user of the medical device 12 on performing certain steps of the self-healing process for the medical device 12.

In some embodiments, non-transitory memory 18 may include components disposed at two or more devices, which may be remotely located and/or configured for coordinated processing. In some embodiments, one or more aspects of non-transitory memory 18 may include remotely-accessible networked storage devices configured in a cloud computing configuration.

User input device 22 may include one or more of a touchscreen, a keyboard, a mouse, a trackpad, a motion sensing camera, or other device configured to enable a user to interact with the medical device 12 and/or the self-healing device 14. In one example, user input device 22 may enable a user to provide an indication of an issue with the medical device or to perform an action recommended by the self-healing device 14 (e.g., to select or to activate a tool).

Display device 24 may include one or more display devices utilizing virtually any type of technology. In some embodiments, the display device 24 may include a computer monitor, and may display information or recommendations related to the self-healing, display data (e.g., images when the medical device 12 is a medical imaging system), or other information. Display device 24 may be combined with the processing system 16, the non-transitory memory 18, and/or the user input device 22 in a shared enclosure, or may be peripheral display devices and may comprise a monitor, touchscreen, projector, or other display device known in the art, which may enable a user to view data (e.g. images produced by medical imaging system) and/or interact with various data stored in the non-transitory memory 18.

The processing system 16 is configured to utilize an autonomous self-healing agent framework, via generative artificial intelligence based reasoning, to detect an issue with the medical device, to locate (e.g., find or determine) an appropriate fix for the issue, and to implement the appropriate fix to resolve the issue. In certain embodiments, the processing system 16 is also configured to the processing system is configured to initiate utilization of the autonomous self-healing agent framework for healing in response to detecting an indicator (e.g., system indicator) of the issue from the medical device via a system bot. In certain embodiments, the processing system 16 is also configured to initiate utilization of the autonomous self-healing agent framework for healing in response to receiving user input, via a user bot, to initiate the utilization.

The processing system 16 is configured to utilize the autonomous self-healing agent framework to access and to utilize tools and functions provided by an original equipment manufacturer of the medical device in a service application program interface in fixing the issue. In certain embodiments, the tools and functions include a detection agent, a recovery agent, and monitors.

In certain embodiments, the processing system 16 is also configured to utilize the autonomous self-healing agent framework to access a knowledge graph and to utilize generative artificial intelligence in reasoning through the knowledge graph to detect the issue with the medical device and to locate (e.g., find or determine) the appropriate fix for the issue. In certain embodiments, nodes of the knowledge graph include service manuals for the medical device, tool descriptions, fault tree analysis, and failure modes and effects analysis.

In certain embodiments, the processing system 16 is configured to utilize the autonomous self-healing agent framework to access a memory when utilizing generative artificial intelligence in reasoning through the knowledge graph to detect the issue with the medical device and to locate (e.g., find or determine) the appropriate fix for the issue. In certain embodiments, the processing system 16 is configured to utilize the autonomous self-healing agent framework to store in the memory a record of detecting the issue with the medical device and fixing the issue. In certain embodiments, the processing system 16 is configured to utilize the autonomous self-healing agent framework to automatically generate a service request when the issue cannot be resolved by the autonomous self-healing agent framework.

Figure 3:
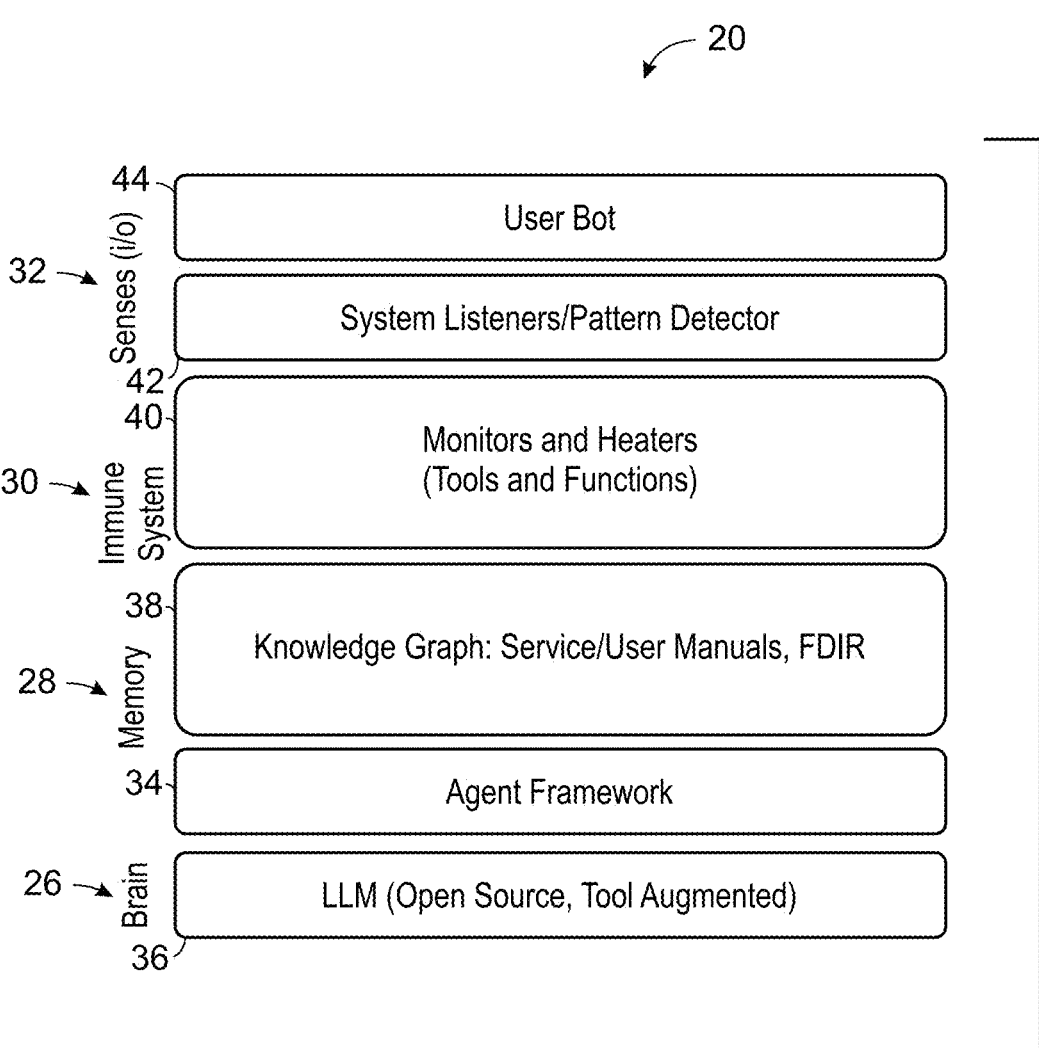
FIG. 3 is a schematic diagram of the self-healing generative AI platform 20 in FIG. 2, in accordance with aspects of the present disclosure.

FIG. 3 is a schematic diagram of the self-healing generative AI platform 20 in FIG. 2. As depicted, the components of the self-healing generative AI platform 20 include a brain 26, a memory 28, an immune system 30, and senses 32 (e.g., inputs/outputs).

The brain 26 (e.g., agent) includes an agent framework 34 (e.g., autonomous self-healing agent framework) and a large language model 36. The agent framework 34 and the large language model 36 are configured to act together to serve as the main controller (e.g., brain) that controls a flow of operations to complete a task or user request (e.g., heal issue with the medical device 12 in FIG. 2). The agent framework 34 is a set of predefined functions compiled into the agent for each resource type. The large language model 36 is a very large deep learning model pre-trained on vast amounts of data. The underlying transformer is a set of neural networks that consist of an encoder and a decoder with self-attention capabilities. The encoder and decoder extract meanings from a sequence of text and understand the relationships between words and phrases in it. The large language model 36 is open sourced and tool augmented. The agent (i.e., the brain 26) is activated in response to a prompt (e.g., user input or query via a user bot) or a system indicator indicative of an issue with the medical device.

The memory 28 includes a knowledge graph 38 including various nodes (e.g., service/user manuals, tool descriptions, fault tree analysis, and/or failure modes and effects analysis) interconnected via particular relationships. The knowledge graph 38 serves as an external knowledge base that provides factual knowledge that keeps the agent (i.e., the brain 26) from hallucinating so that the agent knows what to do. In addition, the knowledge graph 38 assists the agent in planning future actions (i.e., for self-healing of the medical device). The knowledge graph 38 can be a graph data structure having nodes and edges, where nodes represent respective technical features of the medical imaging scanner, and where edges represent respective relations between nodes. The memory 28 stores the agent's internal logs including past thoughts, actions, and observations from the environment (including all interactions between the agent and the user). In particular, the memory 28 also includes a short term memory and a long term memory that manages the agent's past behavior. The short term memory includes context information about the agent's current situation (which is typically realized by in-context learning which means it is short and finite due to the context window constraints). The long term memory includes the agent's past behaviors and thoughts that need to be retained and recalled over an extended period of time. In certain embodiments, the long term memory leverages an external vector store accessible through fast and scalable retrieval to provide relevant information for the agent as needed. In certain embodiments, a hybrid memory of the short term memory and the long term memory may be utilized. The knowledge graph 38 and the short and long term memories allow the agent to operate in a dynamic environment and enable it effectively recall past behaviors and plan future actions.

The immune system 30 includes various monitors and healers 40 (e.g., various tools and functions). Some of these tools may be utilized to identify or to detect an issue (i.e., problem, malfunction, or failure) occurring with the medical device. Some of these tools and functions may be utilized to fix (i.e., repair or heal) an issue with the medical device. Non-limiting examples of tools and functions include a detection agent, a recovery agent, and monitors. These tools and functions may be part of a provided by a service application program interface provided by an original equipment manufacturer of the medical device.

The senses 32 include various inputs and outputs to the self-healing generative AI platform 20. In certain embodiments, the senses 32 include system listeners and/or pattern detectors 42 configured to look for or detect a system indicator of an issue with the medical device. In certain embodiments, the system listeners and/or pattern detectors 42 may initiate, via a system bot, utilization of the self-healing generative AI platform 20 for healing in response to detecting an indicator of an issue from the medical device. The system listeners and/or pattern detectors 42 may be utilized to monitor (or analyze) the medical device for a potential issue or occurring issue. In certain embodiments, the senses 32 include a user bot 44 configured receive a user input (e.g. user query) to initiate utilization of the self-healing generative AI platform 20.

Figure 4:
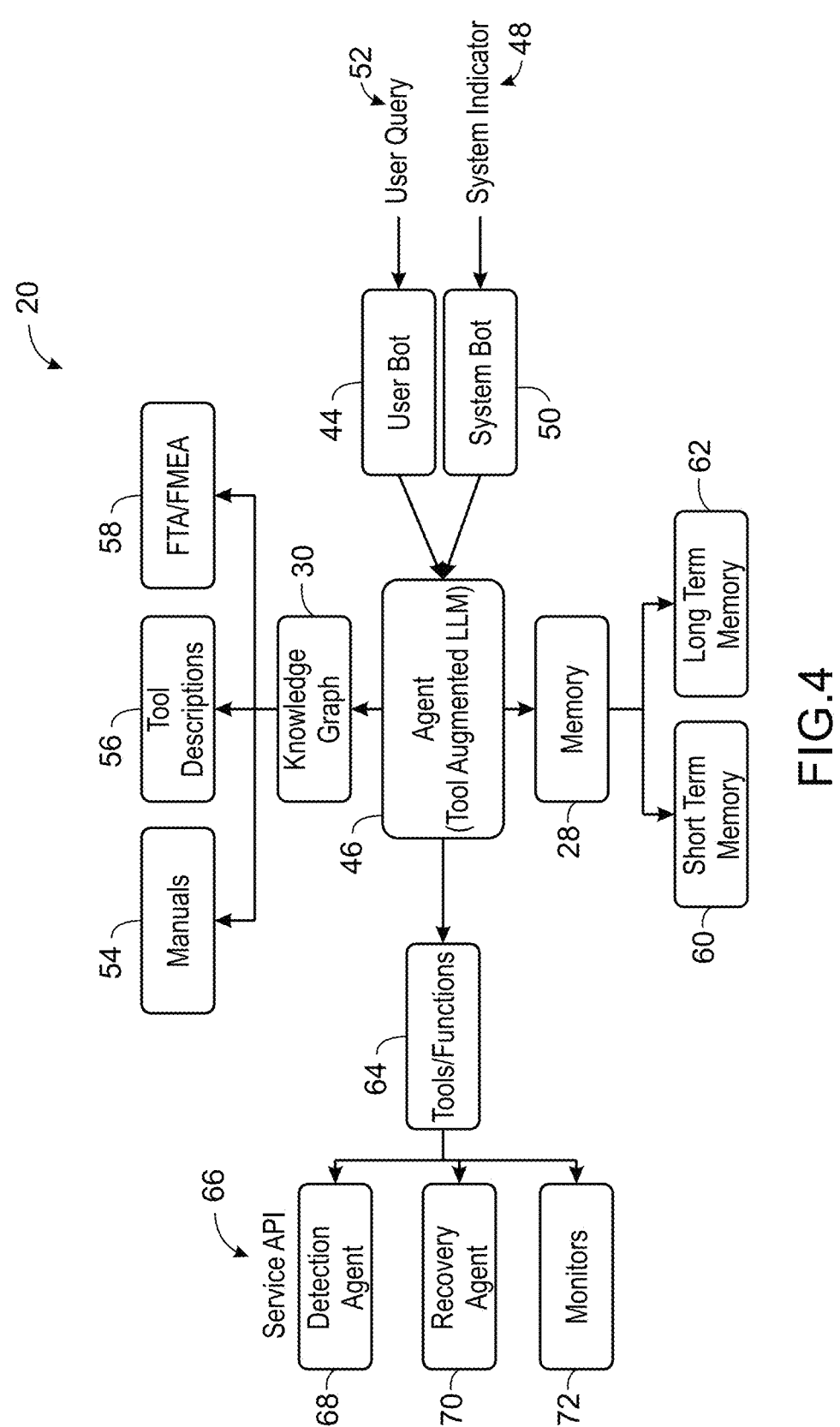
FIG. 4 is a schematic diagram of the interaction between different components of the self-healing generative AI platform in FIG. 2, in accordance with aspects of the present disclosure.

FIG. 4 is a schematic diagram of the interaction between different components of the self-healing generative AI platform 20 in FIG. 2. The self-healing generative AI platform 20 utilizes an autonomous self-healing agent framework configured to utilize generative artificial intelligence based reasoning to detect an issue with the medical device, to locate (e.g., find or determine) an appropriate fix for the issue, and to implement the appropriate fix to resolve the issue. The agent 46 (i.e., brain 26 in FIG. 3) includes a tool augmented large language model.

In certain embodiments, the agent 46 (and, thus, the self-healing generative AI platform 20 or self-healing agent framework) may be activity monitoring for an indication of an issue with the medical device. For example, in certain embodiments, the system listeners and/or pattern detectors detect a potential or occurring issue with the medical device. A system indicator 48 may be provided, via a system bot 50, to the agent 46 to initial utilization of the agent 46 (e.g., self-healing generative AI platform 20) in healing (e.g., self-healing) of the medical device. In certain embodiments, the agent 46 (and the self-healing generative AI platform 20) are activated by the user. In certain embodiments, a user provides an input (e.g., user query 52), via the user bot 44 that initiates utilization of the agent 46 (e.g., self-healing generative AI platform 20) in healing (e.g., self-healing) of the medical device.

Upon initiation of the utilization of the agent 46, the agent accesses both the memory 28 and the knowledge graph 38 in locating (e.g., finding or determining) an appropriate fix for the issue. In certain embodiments, locating an appropriate fixe involves running a diagnostic to determine the cause of the specific issue. The knowledge graph 38 including various nodes (e.g., service/user manuals 54, tool descriptions, and fault tree analysis (FTA) and/or failure modes and effects analysis (FMEA) 58) interconnected via particular relationships. The knowledge graph 38 serves as an external knowledge base that provides factual knowledge that keeps the agent 46 from hallucinating so that the agent 46 knows what to do. In addition, the knowledge graph 38 assists the agent 46 in planning future actions (i.e., for self-healing of the medical device). The fault tree analysis (utilizing a top down approach) maps the relationship between faults, subsystems, and redundant safety elements by creating a logic diagram of the overall system. The undesired outcome is designated as the root (i.e., top event) of a tree of logic. In particular, the fault tree analysis begins with the failure and then diagnoses what could have caused the problem through a series of questions or checks. The failure modes and effects analysis (utilizing a bottom up approach) is a structured way to identify and address potential problems, or failures and their resulting effects on the system or process before an adverse event occurs. In particular, the failure modes and effects analysis looks at each component in turn and creates a list of potential failure modes. The tool descriptions 56 provide description of the various tools that may be utilized by the agent 46 in self-healing the medical device. The service manuals 54 are provided by the original equipment manufacture of the medical device.

The memory 28 stores the agent's internal logs including past thoughts, actions, and observations from the environment (including all interactions between the agent 46 and the user). In particular, the memory 28 also includes a short term memory 60 and a long term memory 62 that manages the agent's past behavior. The short term memory 60 includes context information about the agent's current situation (which is typically realized by in-context learning which means it is short and finite due to the context window constraints). The long term memory 62 includes the agent's past behaviors and thoughts that need to be retained and recalled over an extended period of time. In certain embodiments, the long term memory 62 leverages an external vector store accessible through fast and scalable retrieval to provide relevant information for the agent 46 as needed. In certain embodiments, a hybrid memory of the short term memory 60 and the long term memory 62 may be utilized. The knowledge graph 38 and the short and long term memories 60, 62 allow the agent 46 to operate in a dynamic environment and enable it effectively recall past behaviors and plan future actions.

After determining a plan, the agent 46 may access various tools and/or functions 64 for diagnostics and/or repair. The tools and/or functions 64 may be part of a service application program interface (API) 66 provided by an original equipment manufacturer of the medical device. Examples of the tools and/or functions 64 include a detection agent 68, a recovery agent 70, and/or monitors 72. In certain embodiments, agent 46 is configured to automatically generate a service request when the issue cannot be resolved by the agent 46.

Figure 5:
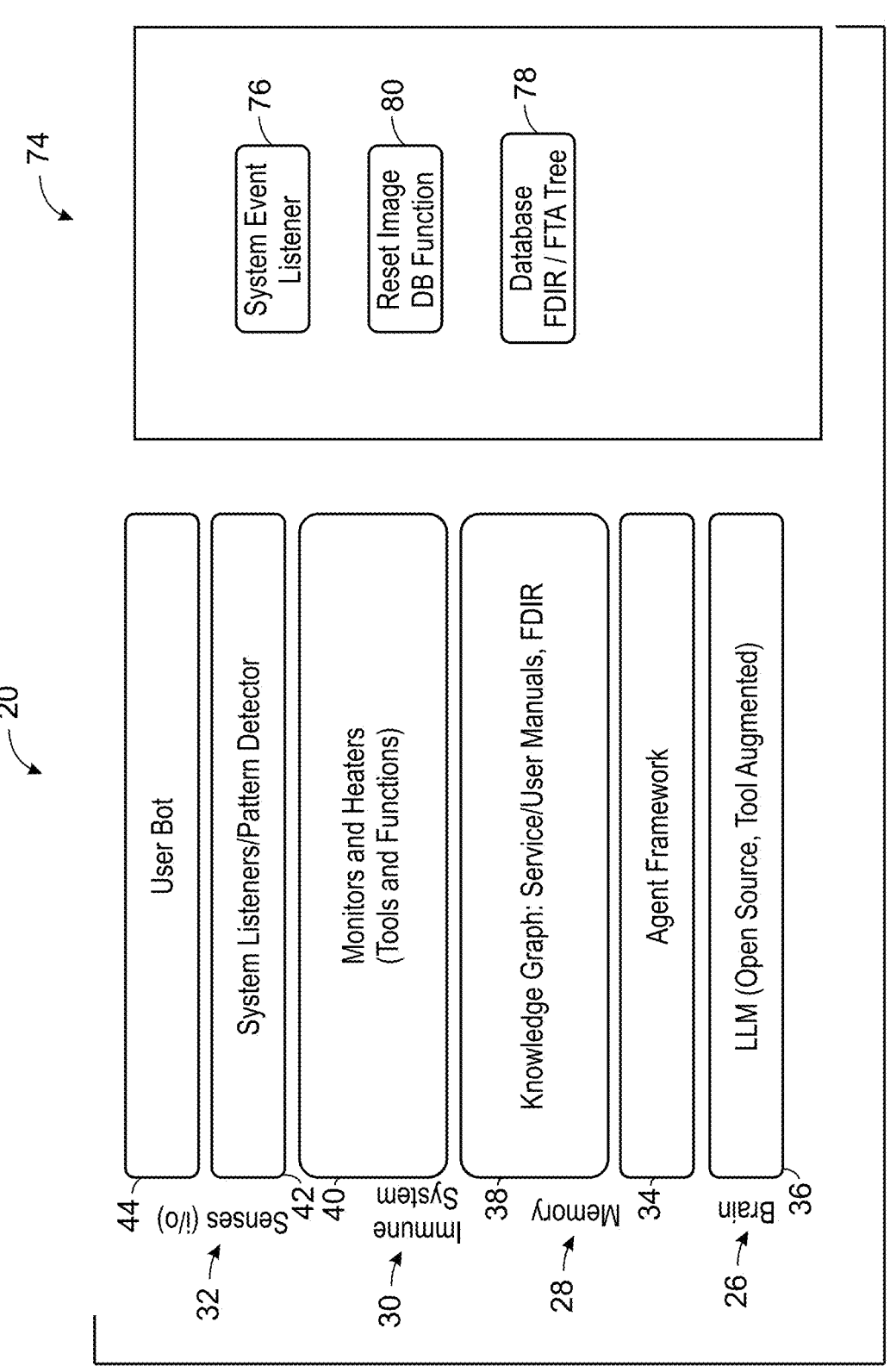
FIG. 5 is a schematic diagram of a first example of a computed tomography imaging use case in which the self-healing generative AI platform in FIG. 2 may be utilized, in accordance with aspects of the present disclosure.
Figure 6:
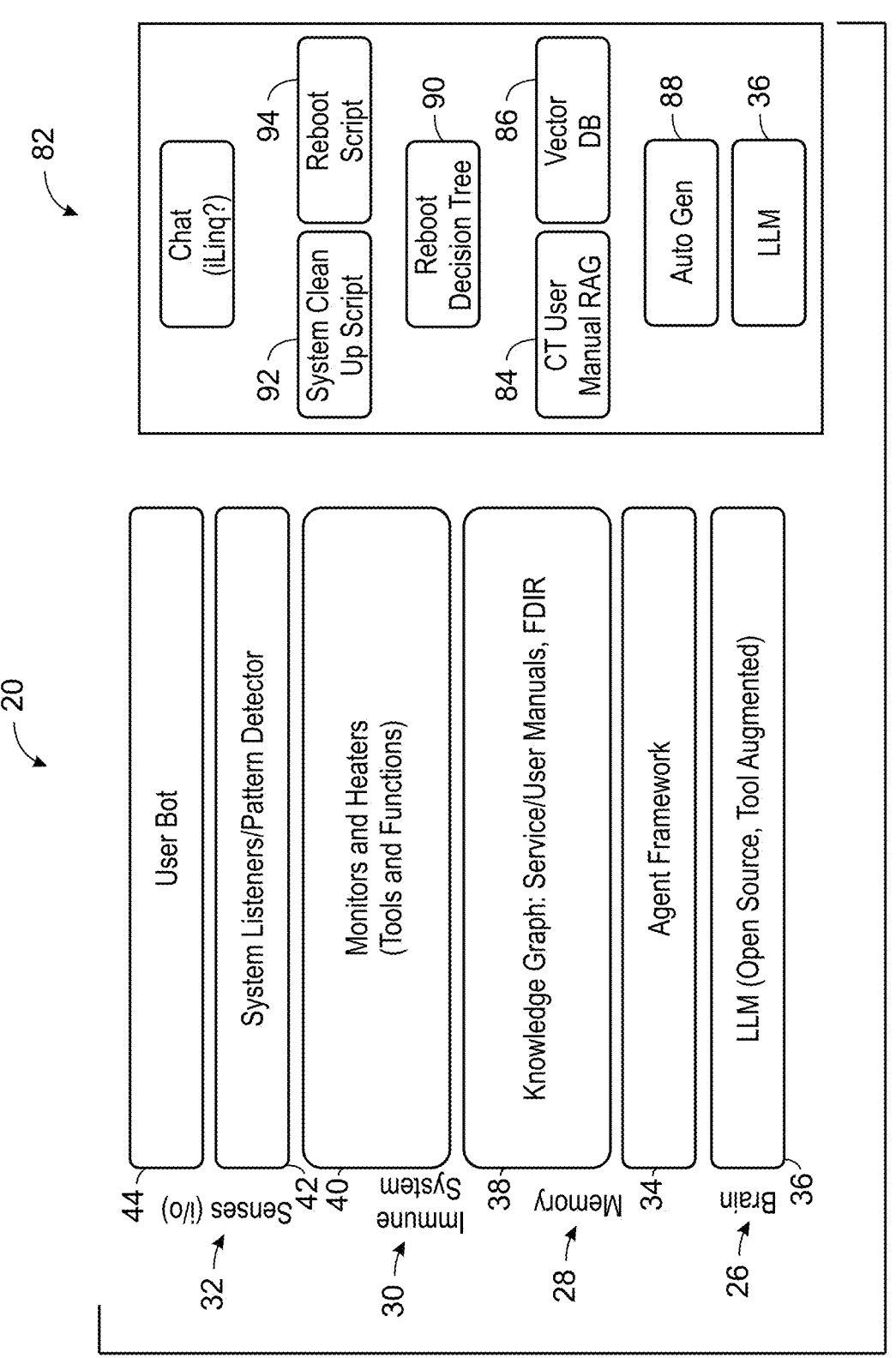
FIG. 6 is a schematic diagram of a second example of a computed tomography imaging use case in which the self-healing generative AI platform in FIG. 2 may be utilized, in accordance with aspects of the present disclosure.
Figure 7:
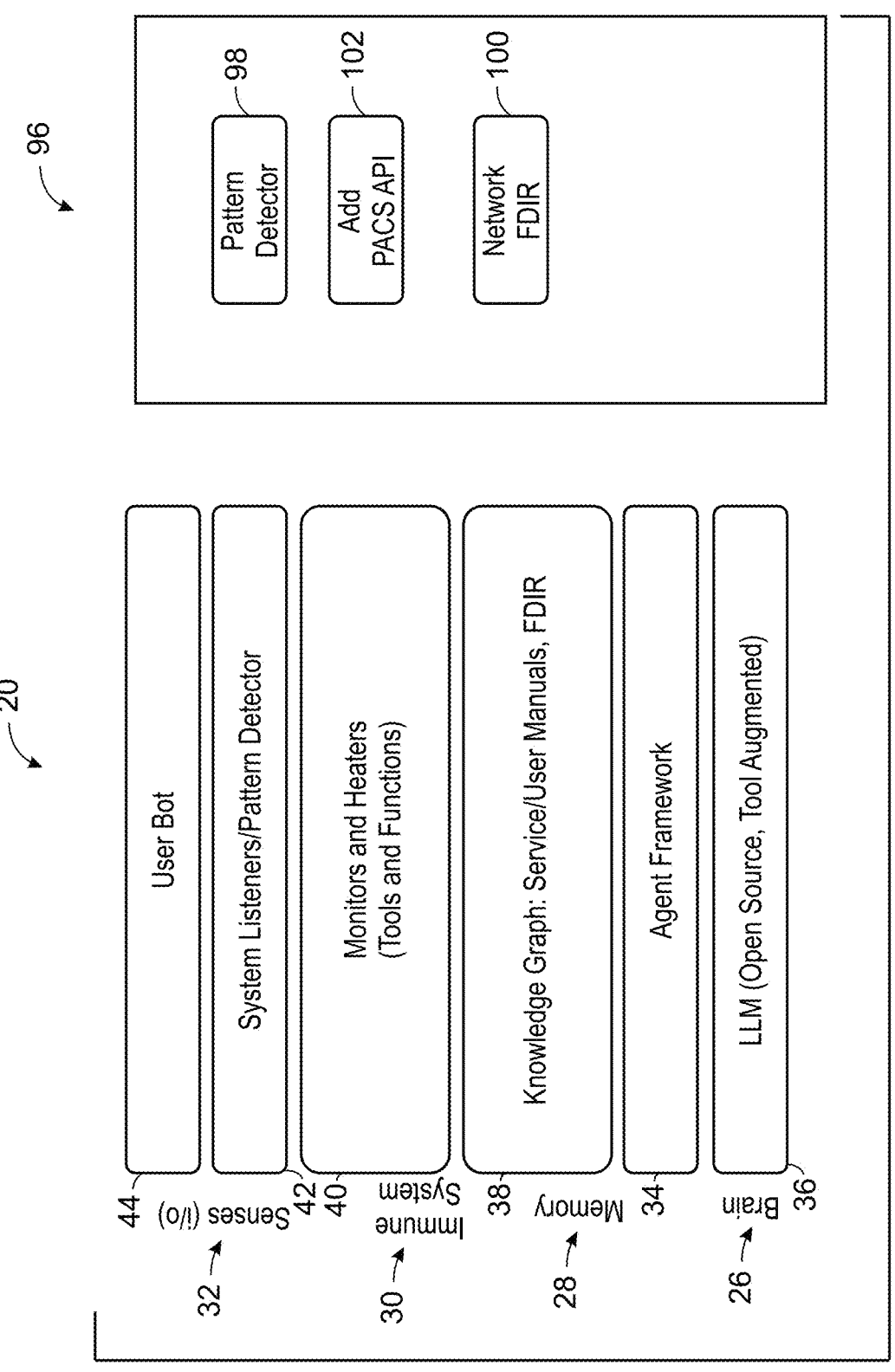
FIG. 7 is a schematic diagram of a third example of a computed tomography imaging use case in which the self-healing generative AI platform in FIG. 2 may be utilized, in accordance with aspects of the present disclosure.

FIGS. 5-7 related to examples of self-healing for a computed tomography console. FIG. 5 is a schematic diagram of a first example 74 of a computed tomography imaging use case in which the self-healing generative AI platform 20 in FIG. 2 may be utilized. As depicted, the specific components of the self-healing generative AI platform 20 utilized for the first example 74 are shown on the right relative to the overall framework of the self-healing generative AI platform 20 shown on the left in FIG. 5. The first example 74 of the computed tomography imaging use case relates to an operator console software database reset. In the first example 74, the self-healing generative AI platform 20 is actively monitoring for an issue. A system indicator of an issue is provided via a system event listener 76. In response to the system indicator, the self-healing generative AI platform 20 performed a fault tree analysis and determined via fault detection, isolation, and recovery (FDIR) that the issue is an issue with an operator console software database as indicated by reference numeral 78. In response to determining the issue, the self-healing generative AI platform 20 performed a function to reset the image database as indicated by reference numeral 80.

FIG. 6 is a schematic diagram of a second example 82 of a computed tomography imaging use case in which the self-healing generative AI platform 20 in FIG. 2 may be utilized. As depicted, the specific components of the self-healing generative AI platform 20 utilized for the second example 82 are shown on the right relative to the overall framework of the self-healing generative AI platform 20 shown on the left in FIG. 6. The second example 82 of the computed tomography imaging use case relates to an operator console full system reboot. In the second example 82, the self-healing generative AI platform 20 is not actively monitoring for an issue. Instead, the self-healing generative AI platform 20 is activated in response to a query from a user via the user bot 44. In response to the query, the tool augmented large language model 36 accessed a computed tomography imaging system user manual and utilized the user input to perform information retrieval (via retrieval-augmented generation (RAG) work) on the user manual as indicated by reference numeral 84. The tool augmented large language model 36 also accessed a vector database (as indicated by reference numeral 86) from the memory to help in retrieving relevant information. In response to accessing and analyzing the user manual and the vector database, the self-healing generative AI platform 20 utilizes an automated generative artificial intelligence (AI) driven self-healing agent 88 to fix the issue (i.e., system reboot). In particular, the self-healing generative AI platform 20 utilized a reboot decision tree in running a system clean up script 92 and a reboot script 94 in performing a reboot of the full system of the operator console.

FIG. 7 is a schematic diagram of a third example 96 of a computed tomography imaging use case in which the self-healing generative AI platform 20 in FIG. 2 may be utilized. As depicted, the specific components of the self-healing generative AI platform 20 utilized for the third example 96 are shown on the right relative to the overall framework of the self-healing generative AI platform 20 shown on the left in FIG. 7. The third example 96 of the computed tomography imaging use case relates to an operator console digital imaging and communications in medicine (DICOM)/network. In the third example 96, the self-healing generative AI platform 20 is actively monitoring for an issue. A system indicator of an issue is provided via a pattern detector 98. In response to the system indicator, the self-healing generative AI platform 20 determined via fault detection, isolation, and recovery (FDIR) that the issue is an issue with an operator console network as indicated by reference numeral 100. In response to determining the issue, the self-healing generative AI platform 20 added a picture archiving and communication systems (PACS) as indicated by reference numeral 102.

Figure 8:
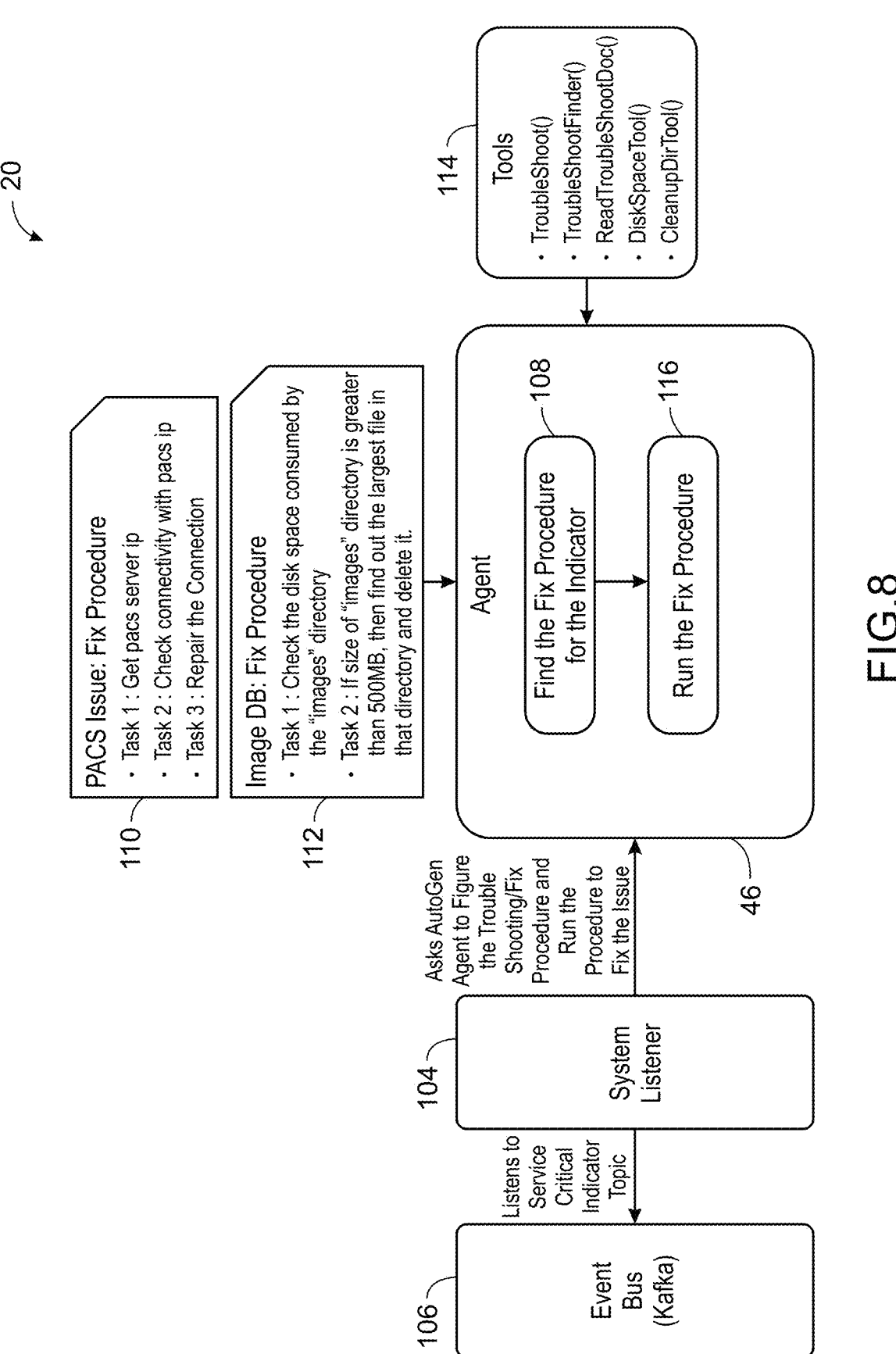
FIG. 8 is a schematic diagram illustrating utilization of a self-healing generative AI platform for performance of a variety of tasks, in accordance with aspects of the present disclosure.

FIG. 8 is a schematic diagram illustrating utilization of the self-healing generative AI platform 20 for performance of a variety of tasks. The self-healing generative AI platform 20 includes the agent 46 (e.g., automated generative artificial intelligence (AI) driven self-healing agent). The agent 46 utilizes a tool augmented large language model. In particular, the agent 46 utilizes a transformer-based model having 2.7 billion parameters. As depicted, a system listener 104 of the self-healing generative AI platform 20 is monitoring an event bus 106 (e.g., listening for a service critical indicator topic). Upon the system listener 104 detecting an issue, it asks the agent 46 to figure out the troubleshooting or fixing procedure and to run the procedure to fix the issue.

The agent 46 accesses a variety of sources (e.g., via a knowledge graph and/or the memory) to find a find a fix procedure for the indicator as indicated by reference numeral 108. For example (as indicated in reference numeral 110), the agent 46 may determine a fix procedure or a PACS issue that may involve a number of tasks: getting the PACS server IP address, checking connectivity with the PACS server IP address, and repairing the connection. In another example (as indicated in the reference numeral 112), the agent may determine a fix procedure for an image database that may involve a number of tasks: checking the disk space consumed by images in the directory and finding and deleting the largest file in that directory (if the size of the images directory is greater than 500 megabytes).

The agent 46 may utilize a variety of tools 114. Non-limiting examples of tools 114 include a troubleshooting tool, a troubleshooting finder tool, a troubleshooting document reader, a disk space tool, and a directory cleanup tool. The agent 46 upon finding the procedure to fix the indicator, then runs the fix procedure as indicated by reference numeral 116.

Figure 9:
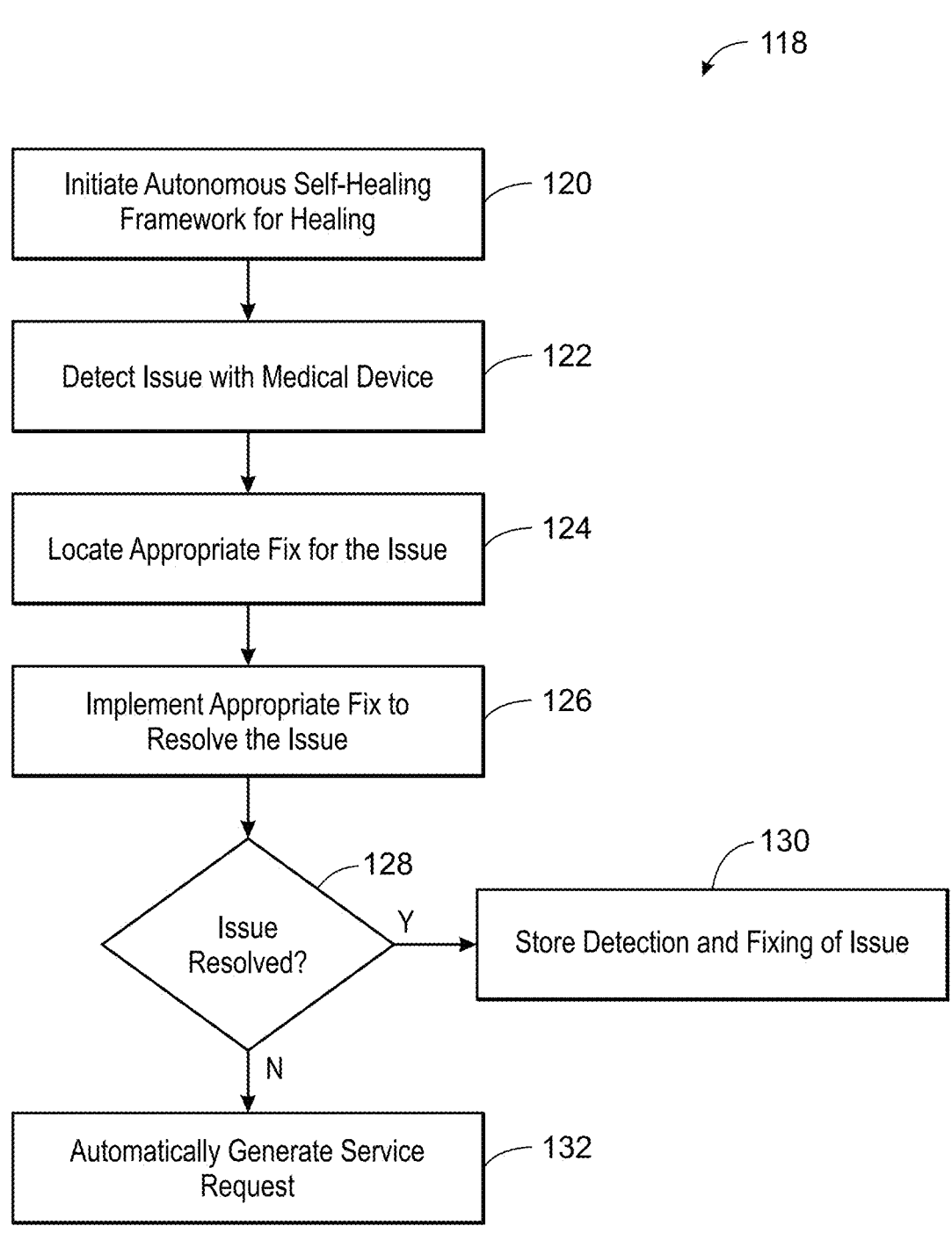
FIG. 9 is a flow chart of a method for self-healing a medical device, in accordance with aspects of the present disclosure.

FIG. 9 is a flow chart of a method 118 for self-healing a medical device. One or more steps of the method 118 may be performed by one or more components of the self-healing device 14 in FIG. 2. One or more steps of the method 118 may be performed simultaneously and/or in a different order from that depicted in FIG. 9.

The method 118 includes initiating utilization of the autonomous self-healing agent framework for healing (e.g., self-healing) of the medical device (block 120). In certain embodiments, the autonomous self-agent framework is actively monitoring the medical device for any indication of an issue. In certain embodiments, the utilization of the autonomous self-healing agent framework for healing is initiated in response to detecting an indicator of the issue from the medical device via a system bot. In certain embodiments, the utilization of the autonomous self-healing agent framework for healing is initiated in response to a user input received via a user bot.

The method 118 also includes utilizing the autonomous self-healing framework to detect an issue with the a medical device (block 122). The method 118 further includes utilizing the autonomous self-healing framework to locate an appropriate fix for the issue (block 124). In certain embodiments, the autonomous self-healing agent framework accesses a knowledge graph (and/or a memory) and utilizes generative artificial intelligence in reasoning through the knowledge graph to detect the issue with the medical device and to locate the appropriate fix for the issue. Nodes of the knowledge graph may include but are not limited to service manuals for the medical device, tool descriptions, fault tree analysis, and failure modes and effects analysis. In certain embodiments, the autonomous self-healing agent framework accesses and utilizes tools and functions provided by an original equipment manufacturer of the medical device in a service application program interface in determining and/or fixing the issue. Tools and function may include but are not limited to a detection agent, a recovery agent, and monitors.

The method 118 further includes utilizing the autonomous self-healing framework to implement the appropriate fix for the issue (block 126). The method 118 even further includes determining if the issue with medical device is resolved (i.e., fixed) (block 128). If the issue with the medical device is resolved, the method 118 includes storing in the memory a record of detecting the issue with the medical device and fixing the issue (block 130). If the issue with medical device is not resolved, the method 118 includes automatically generating a service request for a service/field engineer to come service the medical device (block 132). For example, a service request may be generated when a part of the medical device needs to be replaced.

Figure 10:
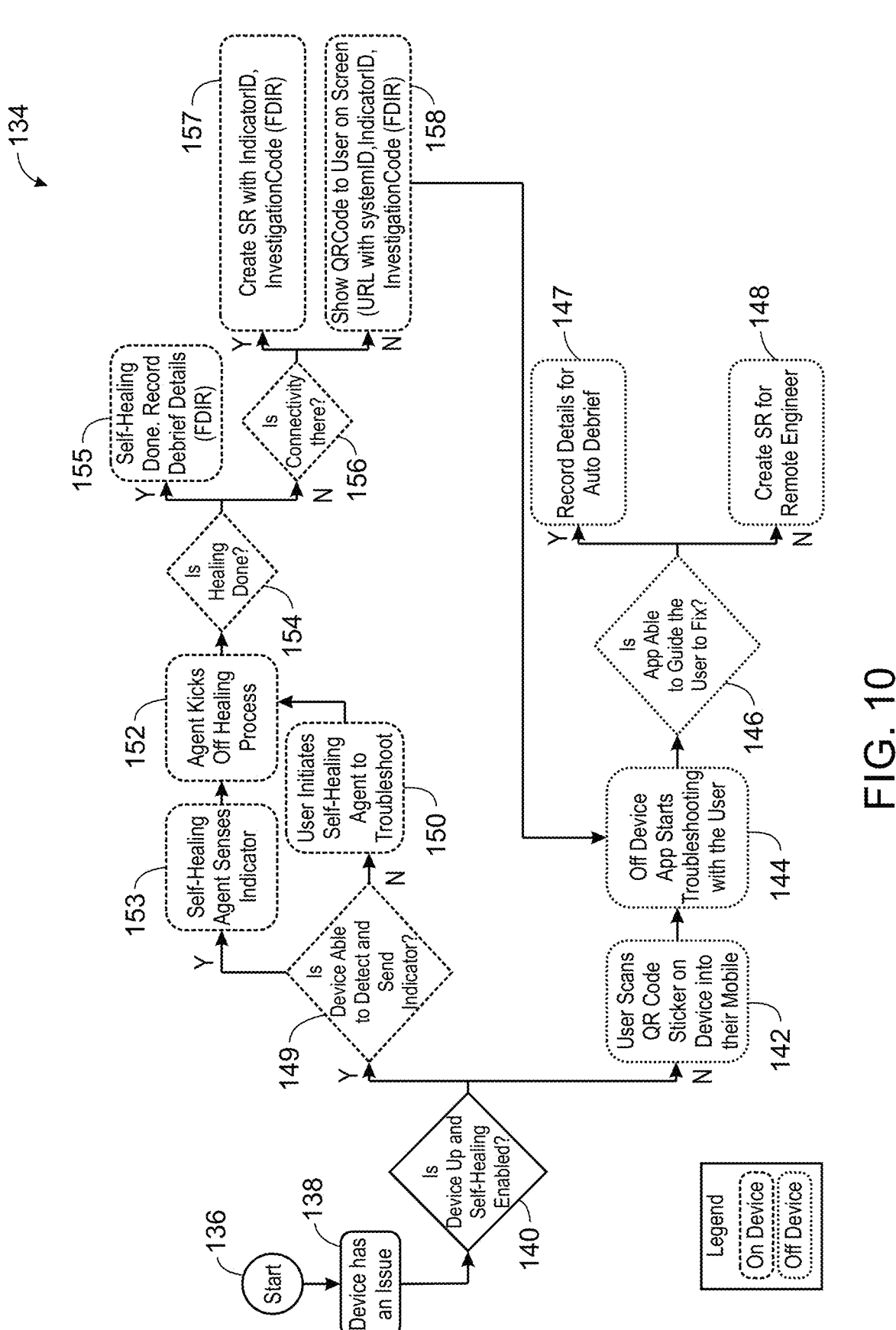
FIG. 10 is a flow chart of a self-healing process, in accordance with aspects of the present disclosure.

FIG. 10 is a flow chart of a self-healing process 134. Upon the starting the process 134 (block 136), a medical device may have an issue (block 138). The self-healing process 134 includes determining if the medical device is up and self-healing enabled (block 140). If the medical device is not up and the self-healing is not enabled, then the self-healing process 134 includes a user scanning a quick response (QR) code sticker on the medical device into their mobile computing device (block 142). Then, the self-healing process 134 includes an off device application starting troubleshooting with the user (block 144). The self-healing process 134 includes determining whether the application is able to guide the user to fix the medical device (block 146). If application is able to guide the user to fix the medical device, the self-healing process 134 includes recording the details for automatic debriefing (block 147). If the application is not able to guide the user to fix the medical device, the self-healing process 134 include creating a service request for a remote engineer to service the medical device (block 148).

If the medical device is up and the self-healing is enabled, then the self-healing process 134 includes determining if the medical device is able to detect and send an indicator (e.g., system indicator) (block 149). If medical device is not able to detect and send an indicator, the self-healing process 134 includes the user initiating the self-healing agent to troubleshoot (block 150) and the self-healing agent kicks off the healing process (block 152). If the medical device is able to detect and send an indicator, the self-healing process 134 includes the self-healing agent sensing the indicator (e.g., system indicator of issue with the medical device) (block 153) and the self-healing agent kicks off the healing process (block 152).

The self-healing process 134 includes determining if the healing of the medical device is done (block 154). If the self-healing is done, the self-healing process 134 includes recording the debriefing details (e.g., FDIR) (block 155). If the self-healing is not done, the self-healing process includes determining if there is connectivity (block 156). If there is connectivity, the self-healing process 134 includes creating a service request (e.g., for a service/field engineer) that includes an indicator identification and an investigation code (block 157). If there is no connectivity, the self-healing process 134 includes showing (e.g., displaying) a QR code to the user on the screen with a uniform resource locator (URL), system identification, indicator identification, and investigation code (block 158).

Figure 11:
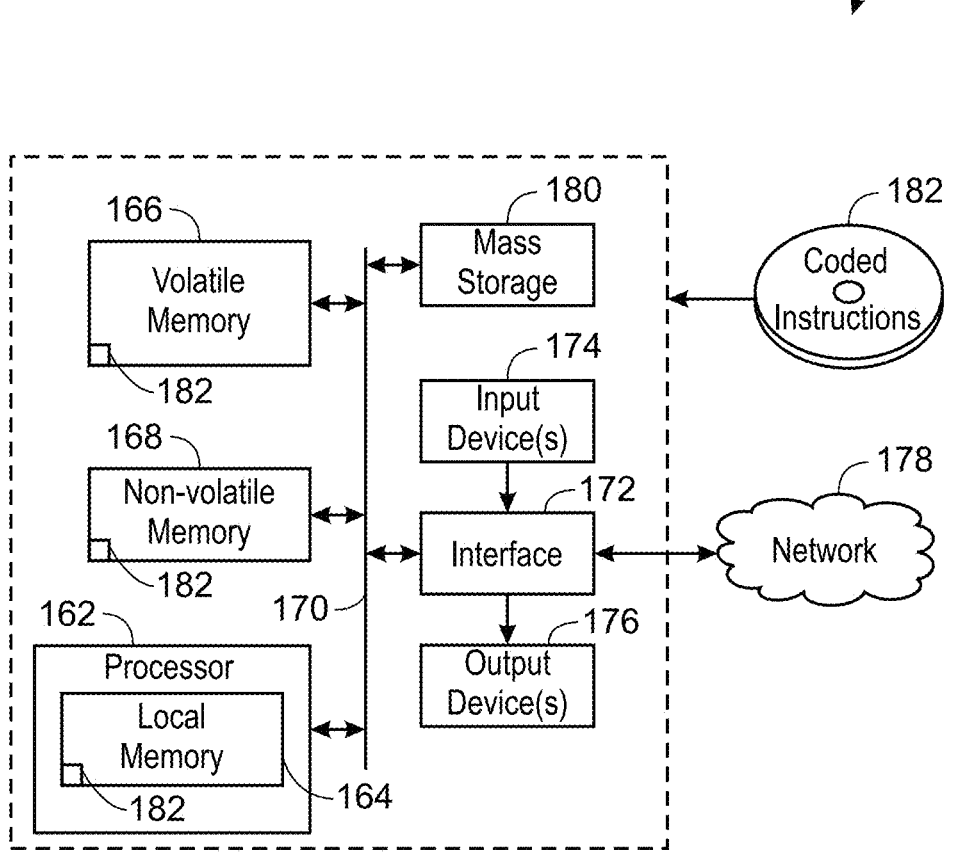
FIG. 11 is a schematic diagram of an example processor platform for a computing device of a medical device to be utilized with the disclosed techniques.

FIG. 11 is a block diagram of an example processor platform 160 for a computing device (e.g., having the self-healing device 14 in FIG. 2) of a medical device to be utilized with the disclosed techniques. The processor platform 160 of the illustrated example includes a processor 162. The processor 162 of the illustrated example is hardware. For example, the processor 162 can be implemented by integrated circuits, logic circuits, microprocessors or controllers from any desired family or manufacturer.

The processor 162 of the illustrated example includes a local memory 164 (e.g., a cache). The example processor 162 of FIG. 10 executes the instructions of at least FIGS. 4 and 5 to implement the systems, infrastructure, displays, and associated methods of FIGS. 4 and 5. The processor 162 of the illustrated example is in communication with a main memory including a volatile memory 166 and a non-volatile memory 168 via a bus 170. The volatile memory 166 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 168 may be implemented by flash memory and/or any other desired type of memory device. Access to the main memory 166, 168 is controlled by a clock controller.

The processor platform 160 of the illustrated example also includes an interface circuit 172. The interface circuit 172 may be implemented by any type of interface standard, such as an Ethernet interface, a universal serial bus (USB), and/or a PCI express interface.

In the illustrated example, one or more input devices 174 are connected to the interface circuit 172. The input device(s) 174 permit(s) a user to enter data and commands into the processor 162. The input device(s) 174 can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 176 are also connected to the interface circuit 172 of the illustrated example. The output devices 176 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 172 of the illustrated example, thus, typically includes a graphics driver card, a graphics driver chip or a graphics driver processor.

The interface circuit 172 of the illustrated example also includes a communication device such as a transmitter, a receiver, a transceiver, a modem and/or network interface card to facilitate exchange of data with external machines (e.g., computing devices of any kind) via a network 178 (e.g., an Ethernet connection, a digital subscriber line (DSL), a telephone line, coaxial cable, a cellular telephone system, Wi-Fi, etc.).

The processor platform 160 of the illustrated example also includes one or more mass storage devices 180 for storing software and/or data. Examples of such mass storage devices 180 include floppy disk drives, hard drive disks, compact disk drives, Blu-ray disk drives, RAID systems, and digital versatile disk (DVD) drives.

Coded instructions 182 may be stored in the mass storage device 180, in the volatile memory 166, in the non-volatile memory 168, and/or on a removable tangible computer readable storage medium (e.g., mass storage device 180).

Technical effects of the disclosed embodiments include providing a generative AI based self-healing agent framework that is located on a medical device and is utilized to self-heal the medical device. Technical effects of the disclosed embodiments also include reducing the downtime of medical device. Technical effects of the disclosed embodiments further include improving service productivity by eliminating the involvement of a remote/field service engineer in fixing the medical device failures. Technical effects of the disclosed embodiments include enabling a medical device to detect an issue and to self-schedule a time for a restart. Technical effects of the disclosed embodiments include enabling a medical device to self-diagnose an issue and to resolve the issue. Technical effects of the disclosed embodiments includes enabling a medical device to assist a user through diagnosing an issue and resolving an issue.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The disclosure also provides support for a medical device, comprising: a memory encoding processor-executable routines, and a processing system comprising one or more processors and configured to access the memory and to execute the processor-executable routines, wherein the processor-executable routines, when executed by the processing system, cause the processing system to: utilize an autonomous self-healing agent framework, via generative artificial intelligence based reasoning, to: detect an issue with the medical device, locate an appropriate fix for the issue, and implement the appropriate fix to resolve the issue. In a first example of the system, the autonomous self-healing agent framework comprises a tool augmented large language model. In a second example of the system, optionally including the first example, the processor-executable routines, when executed by the processing system, further cause the processing system to initiate utilization of the autonomous self-healing agent framework for healing in response to detecting an indicator of the issue from the medical device via a system bot. In a third example of the system, optionally including one or both of the first and second examples, the processor-executable routines, when executed by the processing system, further cause the processing system to initiate utilization of the autonomous self-healing agent framework for healing in response to receiving a user input, via a user bot, to initiate the utilization. In a fourth example of the system, optionally including one or more or each of the first through third examples, the autonomous self-healing agent framework is configured to access and to utilize tools and functions provided by an original equipment manufacturer of the medical device in a service application program interface in fixing the issue. In a fifth example of the system, optionally including one or more or each of the first through fourth examples, the tools and functions comprise a detection agent, a recovery agent, and monitors. In a sixth example of the system, optionally including one or more or each of the first through fifth examples, the autonomous self-healing agent framework is configured to access a knowledge graph and to utilize generative artificial intelligence in reasoning through the knowledge graph to detect the issue with the medical device and to locate the appropriate fix for the issue. In a seventh example of the system, optionally including one or more or each of the first through sixth examples, nodes of the knowledge graph comprise service manuals for the medical device, tool descriptions, fault tree analysis, and failure modes and effects analysis. In an eighth example of the system, optionally including one or more or each of the first through seventh examples, the autonomous self-healing agent framework is configured to access a memory when utilizing generative artificial intelligence in reasoning through the knowledge graph to detect the issue with the medical device and to locate the appropriate fix for the issue. In a ninth example of the system, optionally including one or more or each of the first through eighth examples, the autonomous self-healing agent framework is configured to store in the memory a record of detecting the issue with the medical device and fixing the issue. In a tenth example of the system, optionally including one or more or each of the first through ninth examples, the autonomous self-healing agent framework is configured to automatically generate a service request when the issue cannot be resolved by the autonomous self-healing agent framework.

The disclosure also provides support for a computer-implemented method for a medical device to self-heal, comprising: utilizing, via a processing system comprising one or more processors, an autonomous self-healing agent framework, via generative artificial intelligence based reasoning, to: detect an issue with the medical device, locate an appropriate fix for the issue, and implement the appropriate fix to resolve the issue. In a first example of the method, the autonomous self-healing agent framework comprises a tool augmented large language model. In a second example of the method, optionally including the first example, the method further comprises: initiating, via the processing system, utilization of the autonomous self-healing agent framework for healing in response to detecting an indicator of the issue from the medical device via a system bot. In a third example of the method, optionally including one or both of the first and second examples, the method further comprises: initiating, via the processing system, utilization of the autonomous self-healing agent framework for healing in response to receiving a user input, via a user bot, to initiate the utilization. In a fourth example of the method, optionally including one or more or each of the first through third examples, the method further comprises: utilizing, via the processing system, the autonomous self-healing agent framework to access and to utilize tools and functions provided by an original equipment manufacturer of the medical device in a service application program interface in fixing the issue. In a fifth example of the method, optionally including one or more or each of the first through fourth examples, the method further comprises: utilizing, via the processing system, the autonomous self-healing agent framework to access a knowledge graph and to utilize generative artificial intelligence in reasoning through the knowledge graph to detect the issue with the medical device and to locate the appropriate fix for the issue. In a sixth example of the method, optionally including one or more or each of the first through fifth examples, the method further comprises: utilizing, via the processing system, the autonomous self-healing agent framework to access a memory when utilizing generative artificial intelligence in reasoning through the knowledge graph to detect the issue with the medical device and to locate the appropriate fix for the issue. In a seventh example of the method, optionally including one or more or each of the first through sixth examples, the method further comprises: utilizing, via the processing system, the autonomous self-healing agent framework to automatically generate a service request when the issue cannot be resolved by the autonomous self-healing agent framework.

The disclosure also provides support for a non-transitory computer-readable medium, the computer-readable medium comprising processor-executable code that when executed by a processing system comprising one or more processors, causes the processing system to: utilize an autonomous self-healing agent framework stored on a medical device, via generative artificial intelligence based reasoning, to: detect an issue with the medical device, locate an appropriate fix for the issue, and implement the appropriate fix to resolve the issue.

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical device, comprising:
   a memory encoding processor-executable routines; and
   a processing system comprising one or more processors and configured to access the memory and to execute the processor-executable routines, wherein the processor-executable routines, when executed by the processing system, cause the processing system to:
   initiate utilization of an autonomous self-healing agent framework for healing the medical device in response to detecting an indicator of an issue from the medical device via a system bot of the medical device, wherein the autonomous self-healing agent framework comprises a tool augmented large language model;

utilize the autonomous self-healing agent framework, via generative artificial intelligence based reasoning, to:

detect the issue with the medical device;

locate an appropriate fix for the issue; and implement the appropriate fix to resolve the issue; and wherein the autonomous self-healing agent framework is configured to access a knowledge graph and to utilize generative artificial intelligence in reasoning through the knowledge graph to detect the issue with the medical device and to locate the appropriate fix for the issue, wherein the autonomous self-healing agent framework is configured to access tools, functions, or a combination of tools and functions provided by an equipment manufacturer of the medical device using a service application program interface, and wherein the tools and functions comprise a detection agent, a recovery agent, a monitor, or a combination thereof.

2. The medical device of claim 1, wherein the processor-executable routines, when executed by the processing system, further cause the processing system to initiate utilization of the autonomous self-healing agent framework for healing in response to receiving a user input, via a user bot, to initiate the utilization.

3. The medical device of claim 1, wherein nodes of the knowledge graph comprise service manuals for the medical device, tool descriptions, fault tree analysis, and failure modes and effects analysis.

4. The medical device of claim 1, wherein the autonomous self-healing agent framework is configured to access the memory when utilizing generative artificial intelligence in reasoning through the knowledge graph to detect the issue with the medical device and to locate the appropriate fix for the issue.

5. The medical device of claim 4, wherein the autonomous self-healing agent framework is configured to store in the memory a record of detecting the issue with the medical device and fixing the issue.

6. The medical device of claim 1, wherein the autonomous self-healing agent framework is configured to automatically generate a service request when the issue cannot be resolved by the autonomous self-healing agent framework.

7. A computer-implemented method for a medical device to self-heal, comprising:

initiating, via a processing system comprising one or more processors and located on the medical device, utilization of an autonomous self-healing agent framework for healing the medical device in response to detecting an indicator of an issue from the medical device via a system bot of the medical device;

utilizing, via the processing system, the autonomous self-healing agent framework, via generative artificial intelligence based reasoning, to:

detect the issue with the medical device;

locate an appropriate fix for the issue; and implement the appropriate fix to resolve the issue; and wherein the autonomous self-healing agent framework accesses a knowledge graph and utilizes generative artificial intelligence in reasoning through the knowledge graph to detect the issue with the medical device and to locate the appropriate fix for the issue, wherein the autonomous self-healing agent framework accesses tools, functions, or a combination of tools and functions provided by an equipment manufacturer of the medical device using a service application program interface, and wherein the tools and functions comprise a detection agent, a recovery agent, a monitor, or a combination thereof.

8. The computer-implemented method of claim 7, further comprising initiating, via the processing system, utilization of the autonomous self-healing agent framework for healing in response to receiving a user input, via a user bot, to initiate the utilization.

9. The computer-implemented method of claim 7, further comprising utilizing, via the processing system, the autonomous self-healing agent framework to access a memory when utilizing generative artificial intelligence in reasoning through the knowledge graph to detect the issue with the medical device and to locate the appropriate fix for the issue.

10. The computer-implemented method of claim 7, further comprising utilizing, via the processing system, the autonomous self-healing agent framework to automatically generate a service request when the issue cannot be resolved by the autonomous self-healing agent framework.

11. A non-transitory computer-readable medium, the computer-readable medium comprising processor-executable code that when executed by a processing system comprising one or more processors and located on a medical device, causes the processing system to:

initiate utilization of an autonomous self-healing agent framework for healing the medical device in response to detecting an indicator of an issue from the medical device via a system bot of the medical device;

utilize the autonomous self-healing agent framework stored on a medical device, via generative artificial intelligence based reasoning, to:

detect the issue with the medical device;

locate an appropriate fix for the issue; and implement the appropriate fix to resolve the issue; and wherein the autonomous self-healing agent framework is configured to access a knowledge graph and to utilize generative artificial intelligence in reasoning through the knowledge graph to detect the issue with the medical device and to locate the appropriate fix for the issue, wherein the autonomous self-healing agent framework is configured to access tools, functions, or a combination of tools and functions provided by an equipment manufacturer of the medical device using a service application program interface, and wherein the tools and functions comprise a detection agent, a recovery agent, a monitor, or a combination thereof.

* * * * *